United States Patent [19]
Allman et al.

[11] Patent Number: 5,293,130
[45] Date of Patent: Mar. 8, 1994

[54] PROPORTIONAL COUNTER DEVICE FOR DETECTING ELECTRONEGATIVE SPECIES IN AN AIR SAMPLE

[75] Inventors: Steve L. Allman; Fang C. Chen; Chung-Hsuan Chen, all of Knoxville, Tenn.

[73] Assignee: Martin Marietta Energy Systems, Inc., Oak Ridge, Tenn.

[21] Appl. No.: 724,655

[22] Filed: Jul. 2, 1991

[51] Int. Cl.$^5$ .................. G01N 27/64; H01J 47/04
[52] U.S. Cl. .................. 324/469; 324/465; 250/375
[58] Field of Search .......... 324/464, 469, 465; 250/384, 375

[56] References Cited

U.S. PATENT DOCUMENTS

| | | | |
|---|---|---|---|
| 3,018,376 | 1/1962 | Vanderschmidt | 250/384 |
| 3,803,481 | 4/1974 | Compton et al. | 324/33 |
| 4,007,624 | 2/1977 | Chantry et al. | 73/23 |
| 4,053,825 | 10/1977 | Young | 324/33 |
| 4,063,156 | 12/1977 | Patterson | 324/33 |
| 4,398,152 | 8/1983 | Leveson | 324/465 |
| 4,426,576 | 1/1984 | Hurst et al. | 250/283 |
| 4,435,681 | 3/1984 | Masuda et al. | 324/459 |
| 4,499,054 | 2/1985 | Katsura et al. | 422/98 |
| 4,587,429 | 5/1986 | Tomoda et al. | 250/375 |
| 4,609,875 | 9/1986 | Jeffers | 324/455 |
| 4,769,548 | 9/1988 | Burtscher et al. | 250/423 |

*Primary Examiner*—Gerard R. Strecker
*Assistant Examiner*—Diep Do
*Attorney, Agent, or Firm*—Joseph A. Marasco; Harold W. Adams

[57] ABSTRACT

Apparatus for detecting an electronegative species comprises an analysis chamber, an inlet communicating with the analysis chamber for admitting a sample containing the electronegative species and an ionizable component, a radioactive source within the analysis chamber for emitting radioactive energy for ionizing a component of the sample, a proportional electron detector within the analysis chamber for detecting electrons emitted from the ionized component, and a circuit for measuring the electrons and determining the presence of the electronegative species by detecting a reduction in the number of available electrons due to capture of electrons by the electronegative species.

26 Claims, 2 Drawing Sheets

PROPORTIONAL COUNTER DEVICE FOR DETECTING ELECTRONEGATIVE SPECIES IN AN AIR SAMPLE

The United States Government has rights in this invention pursuant to contract no. DE-AC05-84OR21400 between the United States Department of Energy and Martin Marietta Energy Systems, Inc.

FIELD OF THE INVENTION

The present invention relates to methods and apparatus for detecting small quantities of electronegative species, and more particularly to such methods and apparatus which rely on a proportional counter to measure electron attachment.

BACKGROUND OF THE INVENTION

Chlorofluorocarbon (CFC) heat exchanging compositions, referred to hereinafter as refrigerants, currently used in heat pumps, air conditioners, and refrigerators, are now known to have serious environmental effects due to destructive reactions with ozone in the Earth's atmosphere. It is believed that the chlorine atom in these refrigerants is the "culprit" which leads to the destruction of the ozone layer. Thus, refrigerant containing any chlorine atom as part of its chemical composition will likely be prohibited for use in air conditioners. NonCFC refrigerants which have no Cl atom in their chemical structure, such as fluorocarbons, will likely be used to replace CFC refrigerants currently in use.

It is necessary to locate and repair minute leaks of refrigerants in heat exchanging equipment. Currently available refrigerant leak detectors are generally based on the detection of the chlorine constituent of the molecule. For example, a common CFC leak detector utilizes a small flame impinging upon a copper plate. When CFC is present, the flame will be green in color, due to the chlorine constituent in the CFC.

Other commonly-used detection methods include heated anode and corona suppression. Heated anode leak detectors employ a red-hot platinum and ceramic heater element which releases positive ions. These positive ions are collected on a negatively charged cylindrical cathode to provide a standing current. The presence of CFC in sampled gas increases the emission of positive ions which then triggers the leak signal. The corona suppression leak detector applies a voltage across a sensor element to produce a corona (spark) which generates a standing current. The presence of CFC in sampled gas inhibits the corona spark which triggers a leak signal. Because the use of red-hot elements or sparks raises the possibility of undesired ignition, these types of detectors are not suitable for use in areas where flammable or explosive gas is likely to be present. These detectors are not suitable for detecting chlorine free refrigerants. Also, no intrinsic leak signal amplification appears to be involved in those leak detectors.

A reliable, sensitive, and simple instrument which can be used to detect chlorine-free refrigerant leaks of less than one ounce per year from heat exchange equipment will soon be essential to the heat exchange industry.

Furthermore, awareness of the sensitivity of the environment to the presence of small amounts of hazardous, toxic, or otherwise undesirable materials has created a need for new methods and apparatus for detecting small quantities of these materials in suspect localities. Certain of these materials are comprised of electronegative species, which can form a basis for their detection in very low concentrations. Examples of these materials are polychlorinated biphenyls (PCB's), carbon tetrachloride, and trichloroethylene (TCE). A reliable, sensitive, and simple instrument which can be used to detect one part per million or less of these materials in the atmosphere is essential to the protection of the environment.

OBJECTS OF THE INVENTION

Accordingly, it is an object of the present invention to provide new and improved methods for protecting the environment.

It is another object of the invention to provide a new and improved method and apparatus for detecting refrigerant leaks.

It is a further object of the invention to provide a new and improved method and apparatus for detecting electronegative species.

Further and other objects of the present invention will become apparent from the description contained herein.

SUMMARY OF THE INVENTION

In accordance with one aspect of the present invention, the foregoing and other objects are achieved by apparatus for detecting an electronegative species which comprises:

a proportional counter means including a detection medium capable of being ionized and an electrode extending through the detection medium, the electrode being operated at a positively charged state sufficient to produce gas amplification;

an ionization means for ionizing a portion of the detection medium; and, a circuit means for measuring the quantity of electrons collected at the electrode to determine the presence of an electronegative species by detecting a reduction in the number of available electrons due to capture of electrons by the electronegative species.

In accordance with another aspect of the present invention, apparatus for detecting an electronegative species comprises:

an analysis chamber;

an admitting means communicating with the analysis chamber for admitting a detection medium;

a radioactive source within the analysis chamber for emitting radioactive energy for ionizing a portion of the detection medium;

a proportional counter means within the analysis chamber for detecting electrons emitted from the ionized portion of the detection medium, the proportional counter means including an electrode extending through the detection medium, the electrode being operated at a positively charged state sufficient to produce gas amplification; and, a circuit means for measuring the quantity of electrons collected at the electrode to determine the presence of an electronegative species by detecting a reduction in the number of available electrons due to capture of electrons by the electronegative species.

In accordance with a further aspect of the present invention, a method for detecting an electronegative species comprises the steps of:

providing a proportional counter means including a detection medium capable of being ionized and an electrode extending through the detection medium, the electrode being operated at a positively charged state sufficient to produce gas amplification;

ionizing a portion of the detection medium so that electrons are accelerated toward the electrode to produce the gas amplification; and, measuring the quantity of electrons collected at the electrode to determine the presence of an electronegative species by detecting a reduction in the number of available electrons due to capture of electrons by the electronegative species.

In accordance with a further aspect of the present invention, a method for detecting an electronegative species comprises the steps of:

providing an analysis chamber having an inlet;

providing a radioactive ionization source within the analysis chamber;

providing a proportional counter means within the analysis chamber, the proportional counter means including an electrode extending through the analysis chamber;

introducing through the inlet a detection medium so that radioactive energy from the radioactive ionization source ionizes a portion of the detection medium;

operating the electrode at a positively charged state so that electrons are accelerated toward the electrode to produce gas amplification;

extracting a signal through a capacitor connected to the electrode to measure the quantity of electrons collected at the electrode; and, determining the presence of an electronegative species by detecting a reduction in the number of available electrons due to capture of electrons by the electronegative species.

For a better understanding of the present invention, together with other and further objects, advantages and capabilities thereof, reference is made to the following disclosure and appended claims in connection with the above-described drawing.

DETAILED DESCRIPTION OF THE INVENTION

Many refrigerants have fluorine atoms as part of their chemical compositions. Since compounds containing fluorine tend to have high electron affinity, most refrigerants can easily form negative ions by the process of electron attachment. A proportional counter can be used to detect a small number of electrons due to the amplification of a number of electrons when they are accelerated toward the counter wire which is biased at positive voltage. When an electro-negative species is introduced, most electrons are absorbed, or captured, by these molecules with high electron affinity. Thus, the counting efficiency of the proportional counter is reduced. From the reduction of the counting rate, molecules with high electron affinity, such as refrigerants, can be detected. Electronegative species are defined as compositions that exhibit electron affinity, and more particularly, compositions that are comprised of at least one halogen.

Proportional counters are generally considered to require the use of a counting gas, such as P10 gas (10% $CH_4$ and 90% Ar), as a medium to achieve the amplification process. However, when a source of ionizing energy is associated with a proportional counter, the proportional counter can then be operated in an ambient atmosphere to detect the presence therein of an electronegative species. A preferred embodiment of the invention utilizes a thin wire type proportional counter element attached at or close to the center of a radioactive source. Any radioactive source will produce electron ion pairs in a medium through the decay process. Other sources of ionizing energy may be used, but possibly at greater expense. Electrons are attracted to the wire, which is biased with positive voltage. When electrons are accelerated toward the wire, more electrons will be produced by electron atom collisions; most amplification is achieved in the region which is very close to the wire.

The basic reason proportional counters have heretofore not been considered suitable for use in ambient conditions is the concern of electron attachment to $O_2$ to form $O_2^-$. The large percentage of $O_2$ in air exhibits significant response in attaching to free electrons; hence, intentionally locating the ionizing energy source very close to the wire overcomes the reduction of amplification by $O_2$ sufficiently to allow highly sensitive measurements of compositions which exhibit higher electron affinity. Amplification can, however, be reduced if electron-ion pairs are produced too far from the wire.

Figure 1:
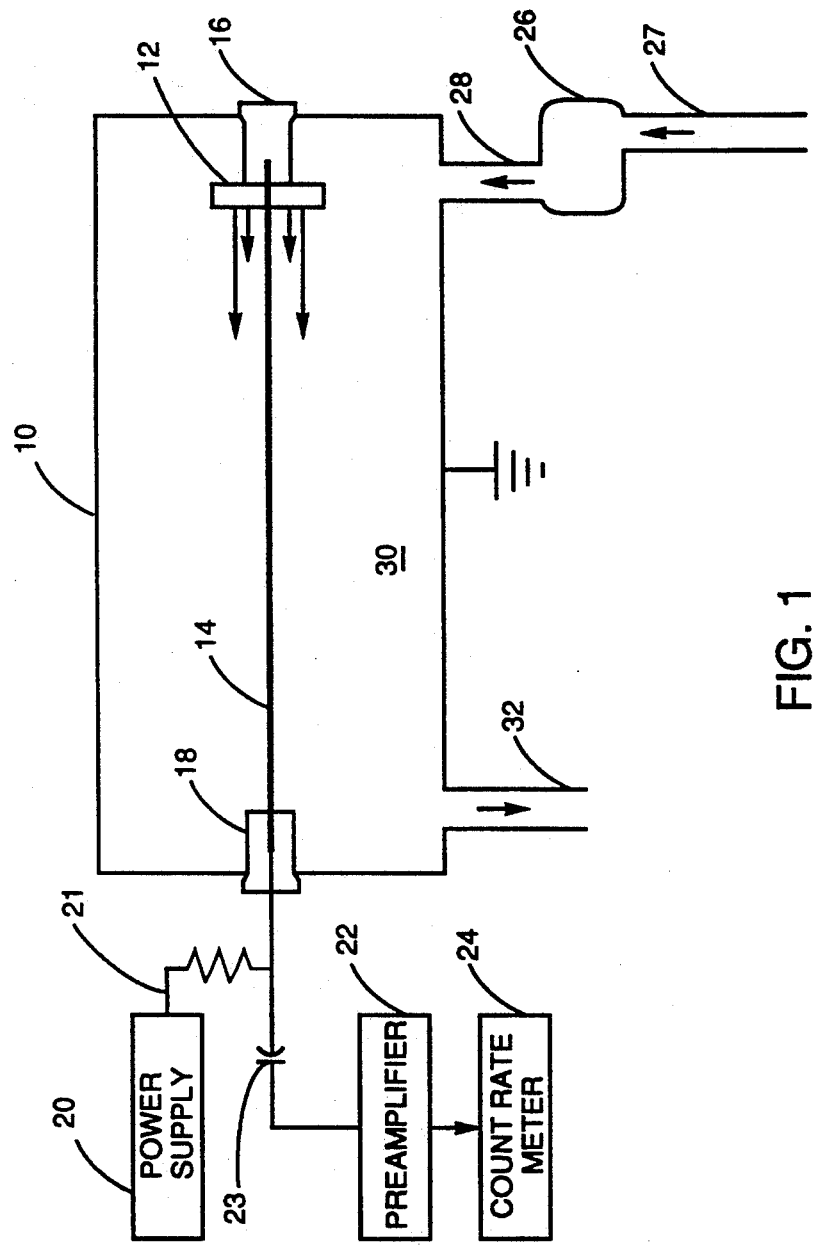
FIG. 1 is a schematic sectional side view of an embodiment of the subject invention.

Referring now to FIG. 1, a proportional counter adapted for detecting small amounts of electronegative species comprises a cylindrical analysis chamber 10 which houses a radioactive source 12, preferably a nominal 1 microcurie α source, at one end and a counter wire 14 suspended between the radioactive source 12 and the other end of the analysis chamber 10. The radioactive source 12 and counter wire 14 are supported by insulating supports 16, 18 attached to the ends of the analysis chamber 10. The counter wire 14 preferably runs centrally and parallel to the greatest cross section of radiation for maximum exposure to available electrons.

The counter wire 14 is a conductor, preferably a metal, and more preferably stainless steel; with a preferred, although not critical diameter of about 0.002 inch. The counter wire 14 is biased at a sufficient voltage, preferably about 100 to about 5000 V, more preferably about 1300 to about 3000 V, most preferably about 1000 to about 2000 V to detect electrons generated by α decay ionization of sample gases. Higher bias voltages generally increase sensitivity, but also increase signal noise, while lower bias voltages generally decrease signal noise, but also decrease sensitivity; the bias voltage should be adjustable in order to optimize conditions for specific analysis situations. The bias voltage is supplied by a power supply 20 connected through a resistor 21, which may have a nominal value of about 23 MΩ, that value not being critical to any particular set of parameters.

A charge sensitive preamplifier 22 amplifies a signal emanating from a capacitor 23 connected to the counter wire 14. The capacitor may have a nominal value of about 0.002 μF, that value not being critical to any particular set of parameters. A count rate meter 24 converts the amplified signal into useful data indicating the number of available electrons within the analysis chamber 10.

An air pump 26 is preferably used to pump sample air or gas from a source through a probe 27 and thence through an inlet 28 and into the analysis chamber 10. An outlet 32 is provided to allow the sample air or gas to pass through the sample chamber 10. Pressures and flow rates are not particularly critical to the operability of the detector. A nominal 1 atm of air is quite satisfactory; there is no critical need for vacuum or high pressure equipment.

The preferred method for using the apparatus involves the detection of electronegative refrigerant leaks from cooling systems.

EXAMPLE I

Figure 2:
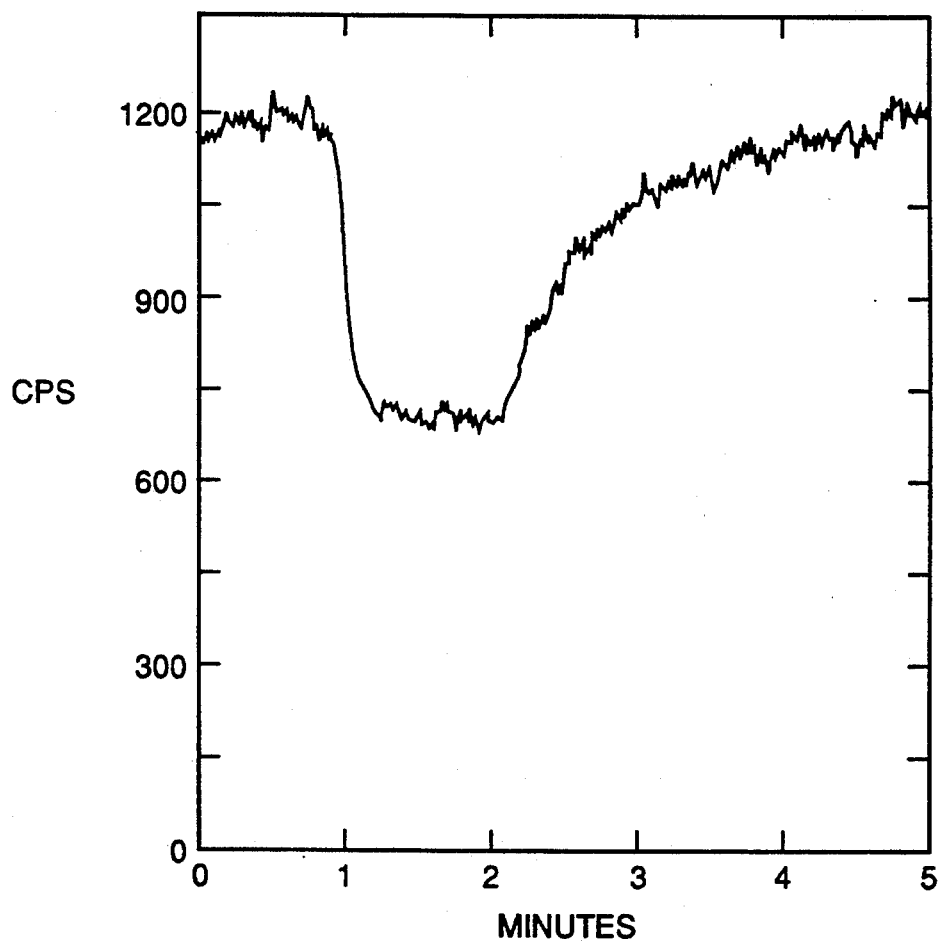
FIG. 2 is a graph representing data collected during a test of the subject invention.

Air was continuously sampled and pumped through the analysis chamber 10. The $\alpha$ source produced electrons and positive ions in the air inside the analysis chamber 10. Electrons produced were accelerated toward the counter wire 14, producing signal pulses which were subsequently amplified by the preamplifier 22 and converted into useful data by the count rate meter 24. A standard counting technique was used to obtain useful counting rate data. Air spiked with an amount of refrigerant R-12 representing a small leak was introduced into the analysis chamber 10. The counting rate dropped due to electron capture by refrigerant molecules, producing a reduced counts-per-second (CPS) signal as shown in FIG. 2. The data presented therein indicate the presence of the refrigerant.

EXAMPLE II

In another experiment similar to that described in Example I, air spiked with a small amount of TCE was introduced into the analysis chamber 10. The counting rate dropped due to electron capture by TCE molecules, producing a negative signal, which indicated the presence of the TCE.

EXAMPLE III

Stack gases from a waste incinerator are continuously introduced into the apparatus. A drop in the counting rate indicates the presence of PCB's or other electronegative species escaping from the incineration process.

Because the fluorine constituent is the most electronegative constituent in refrigerants, it has been demonstrated that the present invention is useful for detecting both chlorine containing chlorofluorocarbon molecules and non-chlorine containing fluorocarbon molecules. The subject apparatus and method are suitable for analyzing samples that contain flammable or explosive constituents because the apparatus and method do not rely on processes which require red-hot elements or sparks which could ignite flammable or explosive gases.

While there has been shown and described what are at present considered the preferred embodiments of the invention, it will be obvious to those skilled in the art that various changes and modifications can be made therein without departing from the scope of the inventions defined by the appended claims.

What is claimed is:

1. Apparatus for detecting the presence of an electronegative species in an air sample comprising:
   a proportional counter comprising an analysis chamber, an electrode extending through said analysis chamber and electrically insulated therefrom, and
   charging means in electrical communication with said electrode for charging said electrode to a positively charged state relative to said analysis chamber, said positively charged state being sufficient to attract toward said electrode electrons produced by ionization of at least a portion of an air sample to produce gas amplification therein;
   an air sampling means in fluid communication with said analysis chamber for admitting an air sample into said analysis chamber;
   an ionization means disposed within said analysis chamber for ionizing at least a portion of the air sample; and,
   a circuit means in electrical communication with said electrode for measuring the quantity of electrons collected at said electrode for determining the presence of an electronegative species in the air sample by detecting a reduction in the number of electrons collected at said electrode, said reduction due to capture of electrons by the electronegative species.

2. The apparatus as defined in claim 1 wherein said ionization means comprises a radioactive source.

3. The apparatus as defined in claim 1 wherein said air sampling means comprises an air pump.

4. The apparatus as defined in claim 1 further comprising a discharge means communicating with said analysis chamber for discharging the air sample from said analysis chamber.

5. The apparatus as defined in claim 1 wherein said ionization means emits ionizing energy along a pathway, and wherein said electrode is located substantially along said pathway.

6. The apparatus as defined in claim 1 wherein said electrode comprises a wire.

7. The apparatus as defined in claim 2 wherein said means for admiting an air sample comprises an air pump.

8. The apparatus as defined in claim 2 further comprising a discharge a discharge means communicating with said analysis chamber for discharging the air sample from said analysis chamber.

9. The apparatus as defined in claim 2 wherein said radioactive source emits radioactive energy along a pathway, and wherein said electrode is located substantially along said pathway.

10. The apparatus as defined in claim 2 wherein said electrode comprises a wire.

11. A method for detecting the presence of an electronegative species in an air sample comprising the steps of:
    providing a proportional counter comprising an analysis chamber, an electrode extending through said analysis chamber and insulated therefrom;
    charging said electrode to a positively charged state relative to said analysis chamber, said positively charged state being sufficient to attract toward said electrode electrons produced by ionization of at least a portion of an air sample to produce gas amplification therein;
    admitting an air sample into said analysis chamber;
    ionizing at least a portion of said air sample to produce electrons which are attracted toward said electrode to produce gas amplification; and,
    measuring the quantity of electrons collected at said electrode to determine the presence of said electronegative species in said air sample by detecting a reduction in the number of electrons collected at said electrode, said reduction due to capture of electrons by said electronegative species.

12. The method as defined in claim 11 wherein said air sample is admitted into said analysis chamber by pumping with an air pump.

13. The method as defined in claim 11 wherein said ionizing step is carried out at ambient pressures.

14. The method as defined in claim 11 wherein said ionizing step is carried out substantially along a pathway defined by said electrode.

15. The method as defined in claim 11 wherein said electrode comprises a wire.

16. The method as defined in claim 11 wherein said electronegative species comprises a halogenated hydrocarbon.

17. The method as defined in claim 11 wherein said electronegative species comprises a refrigerant.

18. The method as defined in claim 17 wherein said refrigerant comprises a fluorinated hydrocarbon.

19. The method as defined in claim 11 wherein said ionization means comprises a radioactive source.

20. The method as defined in claim 19 wherein said air sample is admitted into said analysis chamber by pumping with an air pump.

21. The method as defined in claim 19 wherein said ionizing step is carried out at ambient pressures.

22. The method as defined in claim 19 wherein said ionizing step is carried out substantially along a pathway defined by said electrode.

23. The method as defined in claim 19 wherein said electrode comprises a wire.

24. The method as defined in claim 19 wherein said electronegative species comprises a halogenated hydrocarbon.

25. The method as defined in claim 19 wherein said electronegative species comprises a refrigerant.

26. The method as defined in claim 25 wherein said refrigerant comprises a fluorinated hydrocarbon.

* * * * *